United States Patent [19]

Spiess et al.

[11] Patent Number: 5,364,952
[45] Date of Patent: Nov. 15, 1994

[54] VANADIUM(IV) OXIDE BIS(DIALKYLDITHIOCARBAMATES), PROCESS FOR THEIR PREPARATION, AND OIL COMPOSITIONS CONTAINING THEM

[76] Inventors: Wolfram Spiess, Heinrich-Becker-Strasse 16; Friedrich Franke, Bitzenstrasse 22 A, both of D-6718 both of Grünstadt; Rolf Himmelreich, deceased, late of Grünstadt, Germany, by Margot Marie Charlotte Himmelreich, Petra Himmelreich, heirs; Ralf Himmelreich, heir, Heidelberg-Rohrbach, Germany

[21] Appl. No.: 950,502

[22] Filed: Sep. 25, 1992

[30] Foreign Application Priority Data

Sep. 25, 1991 [DE] Germany ............................ 4131920

[51] Int. Cl.$^5$ ...................... C07F 9/00; C10M 125/00
[52] U.S. Cl. ............................... 556/44; 252/9; 252/35
[58] Field of Search ................. 556/44; 252/9, 35

[56] References Cited

U.S. PATENT DOCUMENTS

| | | | |
|---|---|---|---|
| 3,297,733 | 1/1967 | Kornicker | 260/429 |
| 3,988,249 | 10/1976 | Gencarelli | 252/33.6 |
| 4,381,958 | 7/1987 | Halbert et al. | 556/42 |
| 4,846,983 | 7/1989 | Ward | 252/33.6 |

FOREIGN PATENT DOCUMENTS 2505576 of 1975 Germany .
8707291 12/1987 WIPO .

OTHER PUBLICATIONS

Vigee et al., *J. Inorg. Nucl. Chem.* 1969, vol. 31, pp. 3187–3194 (=Chemical Abstracts, vol. 71 108602c (1969) (Reference A5)).
Chemical Abstracts, vol. 68: 45826u (1968) (Abstract of McCormick, B. J., Inorg. Nucl. Chem. Lett., vol. 3(8), pp. 293–296 (1967)).
Chemical Abstracts, vol. 69, No. 102662j (1968).
Chemical Abstracts, vol. 71, No. 108602c (1969).
Chemical Abstracts, vol. 80, No. 32303u (1974).
Chemical Abstracts, vol. 103, No. 63809m (1985).
Chemical Abstracts, vol. 100, No. 150020d (1984).
Chemical Abstracts, vol. 105, No. 71442t (1986).
Reichel, T. L., et al., Inorganic Chemistry, vol. 15, No. 8, 1976, pp. 1900–1904.

*Primary Examiner*—José G. Dees
*Assistant Examiner*—Porfirio Nazario
*Attorney, Agent, or Firm*—Vorys, Sater, Seymour and Pease

[57] ABSTRACT

Novel vanadium(IV) oxide bis(dialkyldithiocarbamates) of the formula

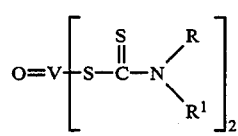

I which R and R$^1$ denote identical or different, branched or straight-chain, saturated or unsaturated alkyl radicals having 1–18 carbon atoms or cycloalkyl radicals having 4–7 carbon atoms, with the proviso that R$^1$ is not identical to R when R is C$_1$–C$_4$-alkyl, cyclobutyl or cyclohexyl, are prepared by a process comprising reacting 2 mols of an alkali metal dialkyldithiocarbamate of the formula

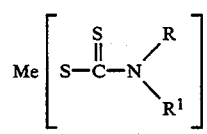

II in which R and R$^1$ are as defined above and Me represents sodium, potassium or ammonium, with 1 mol of vanadium(IV) oxide sulfate pentahydrate in methanol or water as a solvent. The novel vanadium dithiocarbamates can be used as additives for permanent gear lubricating oils or hydraulic fluids to prolong the life of such oils.

7 Claims, No Drawings

VANADIUM(IV) OXIDE BIS(DIALKYLDITHIOCARBAMATES), PROCESS FOR THEIR PREPARATION, AND OIL COMPOSITIONS CONTAINING THEM

BACKGROUND OF THE INVENTION

1. Field of the Invention

This invention relates to vanadium(IV) oxide bis(dialkyldithiocarbamates) as well as to processes for the production of such compounds. The invention also relates to improved lubricating oil and hydraulic fluid compositions containing these compounds.

2. Brief Description of the Prior Art

In accordance with conventional industrial processes, heavy metal dithiocarbamates are prepared either by double displacement reaction of alkali metal or ammonium dithiocarbamates with heavy metal halides or by reaction of metal oxides with amines and carbon disulfide.

However, vanadium dithiocarbamates have not been described hitherto, and it has not been found possible to prepare such compounds by the known industrial methods.

Accordingly, a need has continued to exist to prepare vanadium dithiocarbamates and for a method by which they may be prepared.

SUMMARY OF THE INVENTION

The novel compounds of the invention are vanadium-(IV) oxide bis(dialkyldithiocarbamates) of the formula I

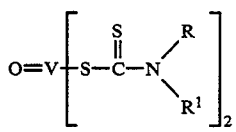

in which R and $R^1$ denote identical or different, branched or straight-chain, saturated or unsaturated alkyl radicals having 1–18 carbon atoms or cycloalkyl radicals having 4–7 carbon atoms with the proviso that $R^1$ must not be identical to R if R is $C_1$–$C_4$-alkyl, cyclobutyl or cyclohexyl.

The compounds of the invention are prepared by reacting alkali metal dialkyldithiocarbamates with vanadium(IV) oxide sulfate pentahydrate. Since the compounds according to the invention possess outstanding properties as oil additives, the preparation thereof represents a substantial improvement over the prior art. The oil additive compounds of the invention have been found to prolong the life of permanent gear lubricating oils and hydraulic fluids to which they are added.

Accordingly, it is an object of the invention to provide vanadium(IV) oxide bis(dialkyldithiocarbamates).

A further object is to provide a method for preparing vanadium(IV) oxide bis(dialkyldithiocarbamates).

A further object is to provide vanadium(IV) oxide bis(dialkyldithiocarbamates) which are useful as additives for lubricating oils and hydraulic fluids.

A further object is to provide lubricating oils and hydraulic fluids having a longer life.

Further objects of the invention will become apparent from the description of the invention which follows.

DETAILED DESCRIPTION OF THE INVENTION AND PREFERRED EMBODIMENTS

The vanadium (IV) oxide bis(dialkyldithiocarbamates) of the invention are prepared by the following reaction scheme:

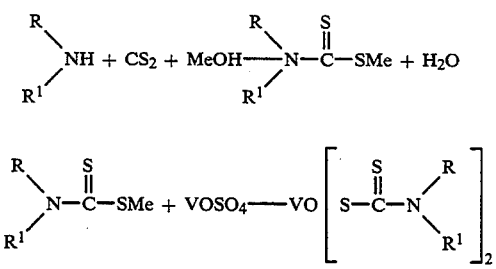

wherein: R and $R^1$ have the signification set forth above, and Me signifies Na, K, or $NH_4$.

The fundamentals of preparing alkali metal dialkyldithiocarbamates are known. In general, the procedure for preparing such compounds is as follows:

A 50% strength sodium hydroxide solution is diluted with a water-miscible solvent, for example methanol, to an NaOH concentration of about 5–10% by weight. A secondary amine is added to this solution and carbon disulfide is added dropwise. All reagents are used in stoichiometric amounts, carbon disulfide preferably being maintained in a 10% excess. The mixture is stirred for 1–3 hours at temperatures of 10°–50° C., preferably at 25° C.

The sodium dialkyldithiocarbamate solution prepared by this procedure can be used directly in further reactions and serves as the starting material for reaction with vanadium(IV) oxide sulfate or another water-soluble vanadium(IV) oxide salt (formerly also termed a vanadyl salt).

Accordingly, in one embodiment of the process of the invention, stoichiometric amounts of vanadium(IV) oxide sulfate pentahydrate are dissolved in water and reacted with the sodium dialkyldithiocarbamate. The reaction takes place at temperatures of 10°–90° C., preferably at 20°–30° C. and more preferably about 30° C.

Instead of methanol, it is also possible to use other watermiscible solvents such as ethylene glycol monoalkyl ether, tetrahydrofuran, dioxane, ethanol, isopropanol, or butanol.

The reaction is weakly exothermic in both steps; consequently, no additional energy has to be supplied.

After a reaction time of 2 hours, the alkali metal sulfate which has precipitated out is filtered off and the mixture of solvent and water is distilled off under vacuum at a temperature of 50° C. If appropriate, sodium sulfate residues are again separated off by filtration from the black-brown oil obtained in this way.

The following examples relating to the preparation of the compounds according to the invention are intended to illustrate the invention but are not to be interpreted as restricting its scope.

EXAMPLE 1

Vanadium(IV) oxide bis(di-2-ethylhexyldithiocarbamate)

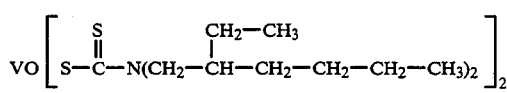

Empirical formula: $C_{34}H_{68}N_2OS_4V$
Molecular weight: 700.103

64 g of a 50% strength sodium hydroxide solution are added to 400 ml of methanol. 192.8 g of di-2-ethylhexylamine are added to this mixture. 50 ml of carbon disulfide are added dropwise over a period of 20 minutes, with mechanical stirring, using a low-temperature condenser.

The mixture is stirred for a further 3 hours. A solution of 100 g of vanadium(IV) oxide sulfate pentahydrate in 250 ml of methanol is then added dropwise over a period of one hour. The mixture is left to stand overnight. The solvent is then evaporated off under vacuum and the residue is taken up in acetone. The sodium sulfate which has precipitated out is filtered off and the acetone is distilled off.

A viscous brown-black oil was obtained.
Yield: 85% of theory, 235.5 g
Purity: by nitrogen determination—94.97%

EXAMPLE 2

Vanadium(IV) oxide bis-(di-2-ethylhexyldithiocarbamate)

32 g of granulated caustic soda are dissolved in 400 ml of anhydrous methanol. 192.8 g of bis-2-ethylhexylamine are added to this solution. 50 ml of carbon disulfide are added dropwise over a period of 20 minutes, with stirring, using a low-temperature condenser. The mixture is stirred for a further 3 hours. A solution of 100 g of vanadium(IV) oxide sulfate pentahydrate in 250 ml of methanol is then added dropwise over a period of one hour. The mixture is left to stand overnight and the sodium sulfate which has precipitated out is filtered off Methanol is then distilled off under vacuum and the product is dried.
Yield: 87% of theory
Purity: by nitrogen determination—97%

EXAMPLE 3

Vanadium(IV) oxide bis(diamyldithiocarbamate)

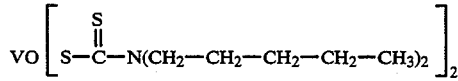

Empirical formula: $C_{22}H_{44}N_2O_4V$
Molecular weight: 531.78

29.6 g of a 50% strength sodium hydroxide solution are added to 200 ml of methanol. 58.1 g of diamylamine are added to this mixture. 24 ml of carbon disulfide are added to the mixture with stirring and the mixture is stirred for a further 2 hours.

47 g of vanadium(IV) oxide sulfate pentahydrate in 150 ml of methanol are then added to the reaction mixture. The mixture is stirred for a further 3 hours and left to stand overnight.

The solvent is distilled off and the residue is taken up in 200 ml of acetone. Sodium sulfate is filtered off and the acetone is distilled off under vacuum. A dark brown oil was obtained.
Yield: 23.2 g Purity: by nitrogen determination—100%

EXAMPLE 4

Vanadium(IV) oxide bis(ditridecyldithiocarbamate)

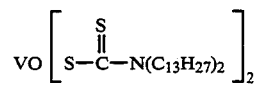

Empirical formula: $C_{54}H_{108}N_2OS_4V$
Molecular weight: 980.640

80 g of a 50% strength sodium hydroxide solution are added to 500 ml of methanol. 381.7 g of ditridecylamine are added to this mixture.

66.5 ml of carbon disulfide are added dropwise over a period of 20 minutes, with mechanical stirring, using a low-temperature condenser. The mixture is stirred for a further 3 hours. A solution of 127 g of vanadium(IV) oxide sulfate pentahydrate in 300 ml of methanol is then added dropwise over a period of one hour. The mixture is left to stand overnight.

The solvent is then evaporated off under vacuum and the residue is taken up in acetone.

Sodium sulfate which has precipitated out is filtered off and the acetone is distilled off. A pasty brown-black product was obtained.
Yield: 80% of theory
Purity: by nitrogen determination—97.5%

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A vanadium(IV) oxide bis(dialkyldithiocarbamate) having the formula I

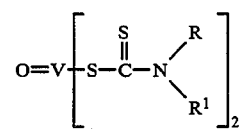

in which R denotes a branched or straight-chain, saturated or unsaturated alkyl radical having 1–18 carbon atoms or a cycloalkyl radical having 4–7 carbon atoms and $R^1$ denotes a branched or straight-chain, saturated or unsaturated alkyl radical having 8–18 carbon atoms.

2. The compound of claim 1, wherein R and $R^1$ are identical or different alkyl radicals having 8–18 carbon atoms.

3. A compound of claim 1 which is vanadium(IV) oxide bis(di-2-ethylhexyldithiocarbamate).

4. A compound of claim 1 which is vanadium(IV) oxide bis(ditridecyldithiocarbamate).

5. A composition of matter comprising an oil selected from the group consisting of permanent gear lubricating oils and hydraulic fluids and a vanadium(IV) oxide bis(dialkyldithiocarbamate) having the formula I

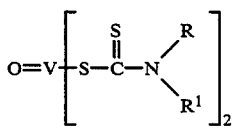

in which R and $R_1$ denote identical or different, branched or straight-chain, saturated or unsaturated alkyl radicals having 1–18 carbon atoms or cycloalkyl radicals having 4–7 carbon atoms, with the proviso that $R^1$ is not identical to R when R is $C_1$–$C_4$-alkyl, cyclobutyl or cyclohexyl.

6. The composition of claim 5 wherein said vanadium(IV) oxide bis(dialkyldithiocarbamate) is present in an amount sufficient to prolong the life of said oil.

7. A method of prolonging the life of an oil selected from the group consisting of permanent gear lubricating oils and hydraulic fluids comprising adding to said oil an amount of a vanadium(IV) oxide bis(dialkyldithiocarbamate) having the formula I

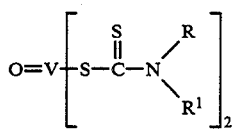

in which R and $R_1$ denote identical or different, branched or straight-chain, saturated or unsaturated alkyl radicals having 1–18 carbon atoms or cycloalkyl radicals having 4–7 carbon atoms, with the proviso that $R^1$ is not identical to R when R is $C_1$–$C_4$-alkyl, cyclobutyl or cyclohexyl, sufficient to prolong the life of said oil.

* * * * *